US010039651B2

(12) United States Patent
Weiss et al.

(10) Patent No.: US 10,039,651 B2
(45) Date of Patent: Aug. 7, 2018

(54) MICROMINIATURE CHAINMAIL INTERFACE BETWEEN SKIN AND A TRANSCUTANEOUS PROSTHETIC DEVICE AND A METHOD OF MANUFACTURE

(71) Applicant: CARNEGIE MELLON UNIVERSITY, Pittsburgh, PA (US)

(72) Inventors: Lee E. Weiss, Pittsburgh, PA (US); Gary K. Fedder, Turtle Creek, PA (US)

(73) Assignee: CARNEGIE MELLON UNIVERSITY, a Pennsylvania Non-Profit Corporation, Pittsburgh, PA (US)

( * ) Notice: Subject to any disclaimer, the term of this patent is extended or adjusted under 35 U.S.C. 154(b) by 0 days.

(21) Appl. No.: 14/996,040

(22) Filed: Jan. 14, 2016

(65) Prior Publication Data
US 2016/0199201 A1     Jul. 14, 2016

Related U.S. Application Data

(60) Provisional application No. 62/125,162, filed on Jan. 14, 2015.

(51) Int. Cl.
| | |
|---|---|
| A61F 2/78 | (2006.01) |
| A61F 2/28 | (2006.01) |
| A61F 2/60 | (2006.01) |
| A61B 17/80 | (2006.01) |
| B22F 3/105 | (2006.01) |
| B33Y 80/00 | (2015.01) |
| B29C 64/153 | (2017.01) |

(Continued)

(52) U.S. Cl.
CPC ............ *A61F 2/60* (2013.01); *A61B 17/8085* (2013.01); *A61F 2/2814* (2013.01); *A61F 2/30728* (2013.01); *A61F 2/78* (2013.01); *B22F 3/1055* (2013.01); *B29C 64/153* (2017.08); *B33Y 80/00* (2014.12); *A61F 2/5046* (2013.01); *A61F 2002/0068* (2013.01); *A61F 2002/30574* (2013.01); *A61F 2002/30914* (2013.01); *A61F 2002/7887* (2013.01)

(58) Field of Classification Search
CPC .......... A61F 2/2814; A61F 2002/30914; A61F 2002/7887
See application file for complete search history.

(56) References Cited

U.S. PATENT DOCUMENTS

| | | | |
|---|---|---|---|
| 5,397,359 A * | 3/1995 | Mittelmeier ......... | A61C 8/0012 623/1.5 |
| 8,257,435 B2 | 9/2012 | Pitkin et al. | |

(Continued)

*Primary Examiner* — David H Willse
(74) *Attorney, Agent, or Firm* — Michael G. Monyok; David G. Oberdick

(57) ABSTRACT

The disclosure describes a direct skeletal attachment (DSA) device including a micro-miniature chainmail skin-to-DSA interface. The interface comprises various porous architectures for skin ingrowth and integration as barriers against pathogens. Failure of skin-to-DSA interfaces can occur due to mismatches in mechanical compliance between pliable skin and more rigid DSA interfaces. To address this problem, in embodiments disclosed herein is an interface having a gradient in mechanical compliance or link mobility, ranging from fully flexible, to less compliant, to rigid where it attaches to the main DSA body.

8 Claims, 9 Drawing Sheets

(51) Int. Cl.
    *A61F 2/50*         (2006.01)
    *A61F 2/30*         (2006.01)
    *A61F 2/00*         (2006.01)

(56) References Cited

U.S. PATENT DOCUMENTS

| | | |
|---|---|---|
| 2004/0068324 A1 | 4/2004 | Grundei |
| 2005/0102038 A1 | 5/2005 | Grundei |
| 2006/0041318 A1 | 2/2006 | Shannon |
| 2007/0060891 A1* | 3/2007 | Skiera ............... A61F 2/2814 604/175 |
| 2007/0073412 A1 | 3/2007 | Blunn et al. |
| 2008/0200995 A1 | 8/2008 | Sidebotham |
| 2009/0036908 A1 | 2/2009 | Zokol et al. |
| 2009/0149966 A1 | 6/2009 | Blunn et al. |
| 2011/0190907 A1 | 8/2011 | Porter et al. |
| 2013/0337724 A1 | 12/2013 | Porter et al. |
| 2014/0081422 A1 | 3/2014 | Hugate |
| 2014/0107806 A1 | 4/2014 | Blunn et al. |
| 2014/0156022 A1 | 6/2014 | Holt et al. |
| 2014/0195002 A1 | 7/2014 | Bachus et al. |
| 2014/0214177 A1 | 7/2014 | Porter et al. |
| 2014/0276454 A1 | 9/2014 | Kuiken et al. |
| 2015/0289978 A1 | 10/2015 | Fitzpatrick |

\* cited by examiner

MICROMINIATURE CHAINMAIL INTERFACE BETWEEN SKIN AND A TRANSCUTANEOUS PROSTHETIC DEVICE AND A METHOD OF MANUFACTURE

CROSS-REFERENCE TO RELATED APPLICATIONS

This application claims the benefit under 35 U.S.C. § 119 of Provisional Ser. No. 62/125,162, filed Jan. 14, 2015, which is incorporated herein by reference.

STATEMENT REGARDING FEDERALLY SPONSORED RESEARCH

Not applicable.

BACKGROUND OF THE INVENTION

The invention relates generally to transcutaneous prosthetic devices. More specifically, the invention relates to an interface between a transcutaneous prosthesis and the skin of a patient.

Approximately two million persons were living with limb loss in the United States in 2007. The main causes of limb loss are vascular disease (54%), including diabetic vasculopathy and peripheral arterial disease, trauma (45%), and cancer (less than 2%). As a result, approximately 185,000 amputations occur in the United States each year.

Limb prostheses, which are used to recover some functionality, are typically mated to the residual stump (residuum) of amputated limbs using custom conformal sockets. Socket attachment can be achieved by creating a vacuum between the residuum and the prosthesis. As the patient dons the prosthesis, air is expelled from the socket through a one-way valve. The negative pressure around the residuum holds the prosthesis in place until the user releases it by opening the valve. The socket attachment method is not an ideal solution. Problems include: phantom pain due to loss of osseoperception; difficulty in properly attaching the prosthesis from changes in skin condition and/or residuum volume; difficulty fitting short residuums; skin irritation; lack of robust stabilization between the prosthesis and residual limb; and, in general, difficulties from frequently donning and doffing the socket.

Direct skeletal attachment (DSA) is an alternative method of prosthesis attachment that can provide osseoperception, improved locomotor activities of a patient, and elimination of other problems associated with donning and using a socket. In the DSA approach an intramedullary stem integrates with intact bone, and a percutaneous pylon attached to the stem acts as a mounting post for the prosthesis. See, for example, U.S. Pat. No. 3,947,897, which describes an apparatus for connecting a prosthesis to a bone of a residuum.

Because the DSA implant protrudes through the skin of the patient, DSA implants are susceptible to infections. To address this issue, DSA implants incorporate skin-to-DSA interfaces comprising various porous architectures for skin ingrowth and implant cutaneous integration as barriers against pathogens traveling down the pylon down to the stem and the surrounding tissues, in particular bone. However, current skin-to-DSA interfaces often fail, leading to infection and implant instability, requiring DSA device removal and replacement either with another DSA implant or more conventional socket suspension system.

Skin-to-DSA interface failures can occur due to the mismatch in mechanical compliance between pliable skin and the more rigid DSA interface or the DSA device itself, which are often composed of titanium alloys such as Ti-6Al-4V. This mismatch can lead to stress risers that cause the skin to tear away from the interface as the skin moves relative to the bone during normal motion or as the recipient gains or losses weight. To minimize tearing, it is thought that the mobility of skin around the implant should be minimized; both surgical techniques and devices for this purpose have been developed.

Devices attempting to solve this problem include a percutaneous bar with a flexible mesh collar, holes at the subcutaneous perimeter of a flange, and a collar made of a stainless steel spring or nylon hooks. Animal studies with these devices produced promising results, however, many of the implants are sensitive to its positioning relative to the dermal and subcutaneous tissues and do not tolerate junction shifting when the distance from the bone to the skin-binding junction changes. Another approach was positioning of a bar with a porous flange in the dermal tissues immediately below the epithelium. While this may reduce the mobility of skin in the plane parallel to the flange, the attachment to the solid bar still remained fragile. In another device, an interface design provides a dome-shaped device with holes for skin attachment; however, the interface is rigid and therefore does not address the problem of compliance mismatch.

When the skin at the skin-to-DSA interface tears, it creates entry points for bacteria and other pathogens into the body. Tears can self-repair by reepithelization, but the repairs are weaker after each tear. For example, recurring atrophic or hyper-trophic scarring and callus formation at the skin-to-implant interface will incrementally reduce the strength of the tissue adhesion in subsequent repairs, thus spiraling into weaker dermal and epidermal integration and thereby increase the risk of further tears and infection. While the initial clinical studies using DSA limb prostheses in humans were conducted in the U.S. in the mid 1970's, the FDA does not currently allow DSA procedures, in part because of a lack of compelling evidence for a solution to the skin seal problem.

Despite these problems, DSA prosthetic devices are permitted in other countries. Over 150 patients in Sweden, Germany, the Netherlands, and Australia have received DSA devices, and analysis and in-depth interviews with patients living with osseointegrated prostheses objectively confirmed functional improvements. Participants described their experience with DSA prostheses as making a revolutionary change to the quality of their lives. However, improved DSA interfaces are still required to minimize infection and reduce the need or surgical removal or periodic replacement of the DSA device. It would therefore be advantageous to develop a DSA interface that reduces skin tearing.

BRIEF SUMMARY OF THE INVENTION

According to embodiments of the present disclosure is an improved skin-to-DSA interface. In one embodiment, the interface comprises chainmail having a gradient in mechanical compliance, mobility, and porosity. Interconnected links of the chainmail have varying inner diameters and spacing, which affect the compliance, mobility, and porosity characteristics.

Further disclosed is a method of manufacturing the interface using additive manufacturing techniques. In one embodiment, neighboring links are fused to create a stable base on which to create additional layers of the interface. In this embodiment, an etching step is used to free the links upon completion of the additive manufacturing steps. Etching can also be used to create the differentiations in mechanical compliance, mobility, and porosity.

DETAILED DESCRIPTION OF THE INVENTION

Figure 1:
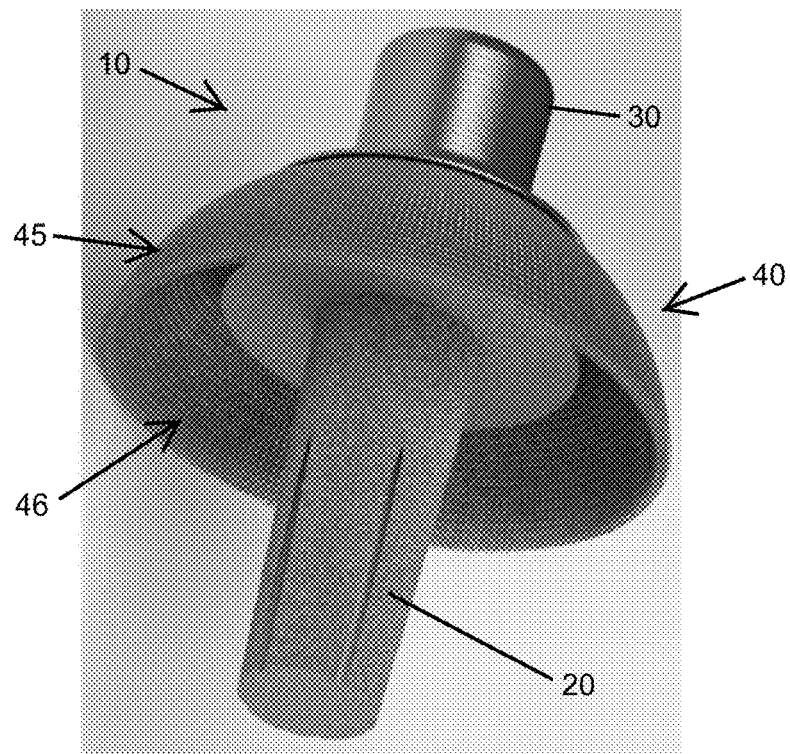
FIG. 1 is a rendering of the interface as part of a DSA device according to one embodiment.

In one embodiment, a direct skeletal attachment (DSA) device 10 comprises an intramedullary stem 20, a post 30, and an interface 40 positioned between the stem 20 and post 30. The intramedullary stem 20 is shaped to be inserted in the intramedullary space in bone (such as the femur) at the site of an amputation. The post 30 is shaped for attachment to an artificial limb or other prosthesis. As shown in FIG. 1, the post 30 is round and relatively short. However, the shape and size can be configured differently depending on the attachment mechanism of the artificial limb being attached to the post 30.

The interface 40 comprises a series of interconnected links 41, which form a micro-miniature chainmail scaffolding 42. Because the links 41 are in direct contact with tissue, they are made of a biomaterial that is both biocompatible and durable. In one configuration, the links 41 are constructed from a titanium alloy. In alternative embodiments, a cobalt-chrome alloy is used. The inner diameters of the chainmail links 41 are approximately 1 mm or less.

Figure 2:
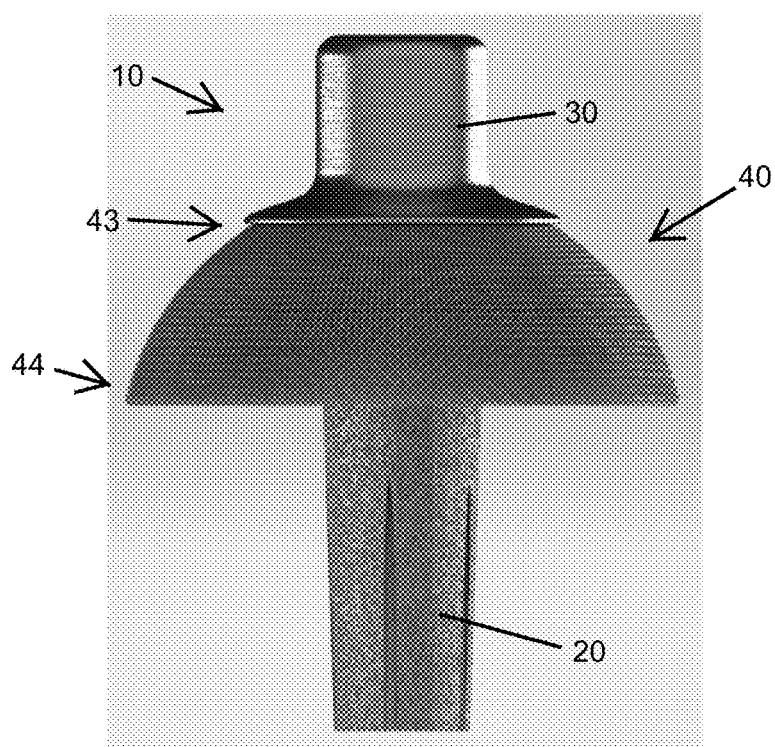
FIG. 2 is an alternate view of the device showing the interface, including the inner surface and outer surface of the interface.
Figure 3:
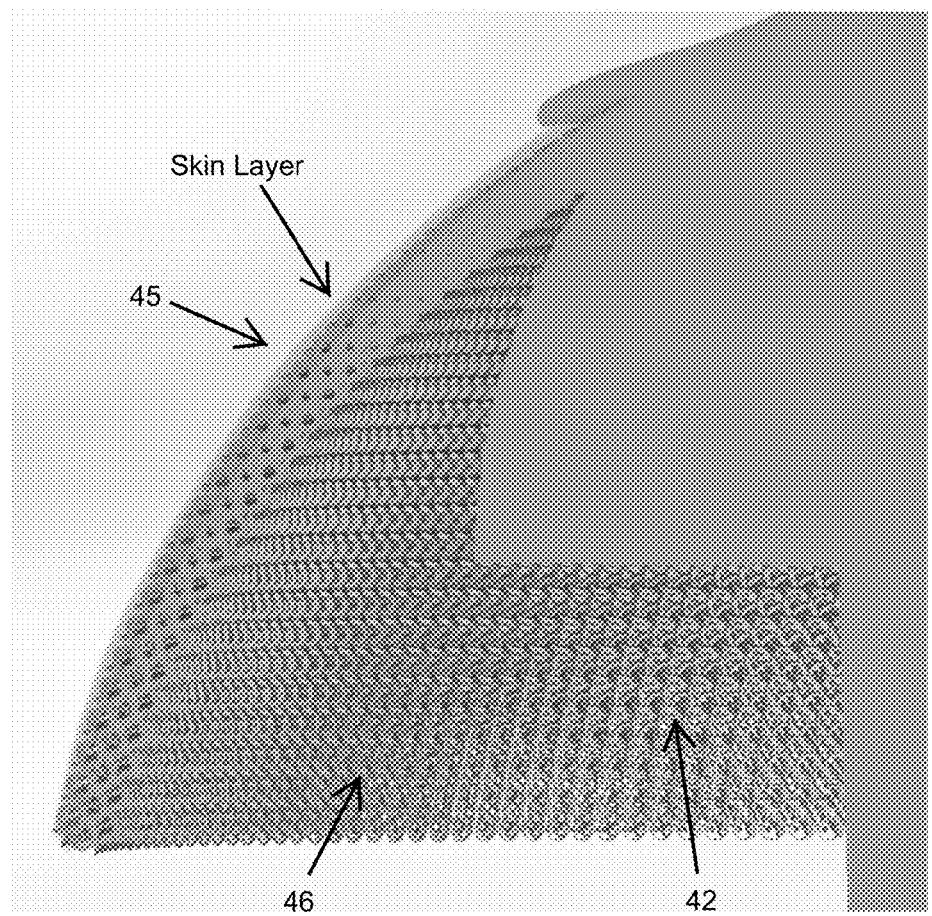
FIG. 3 is a detailed view of the chainmail structure of the interface according to one embodiment.

As shown in FIG. 2, the interface 40 is dome-shaped, with the interface 40 centered around a common axis shared with the stem 20 and post 30. However, the interface 40 is not limited to a dome shape and can be adjusted to conform to the contours of the end of the residuum. As such, a person having skill in the art will appreciate that the interface 40 can have a variety of shapes, which can be achieved by varying the spacing and size of the links 41. As shown in FIG. 3, skin grows on the outside surface 45 of the interface 40 up to the post 30.

Figure 4A:
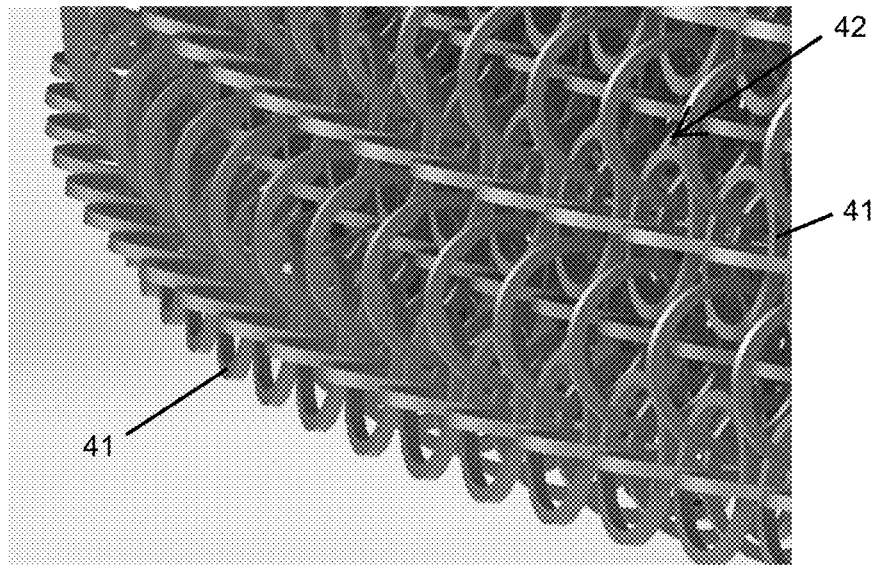
FIGS. 4A, 4B, and 4C show the relative dimensions of the links in different regions of the interface.
Figure 4B:
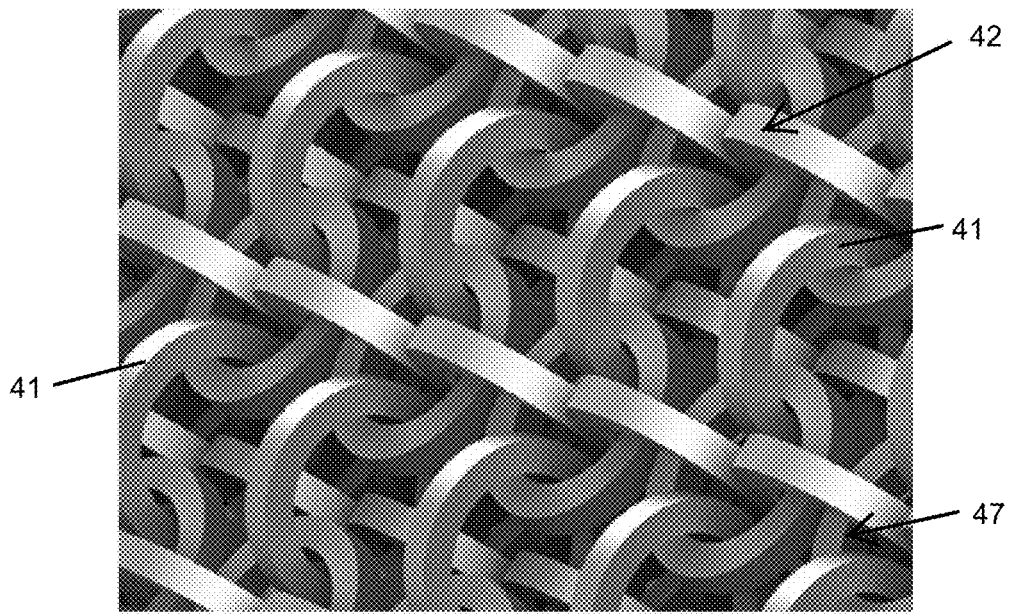
Figure 4C:
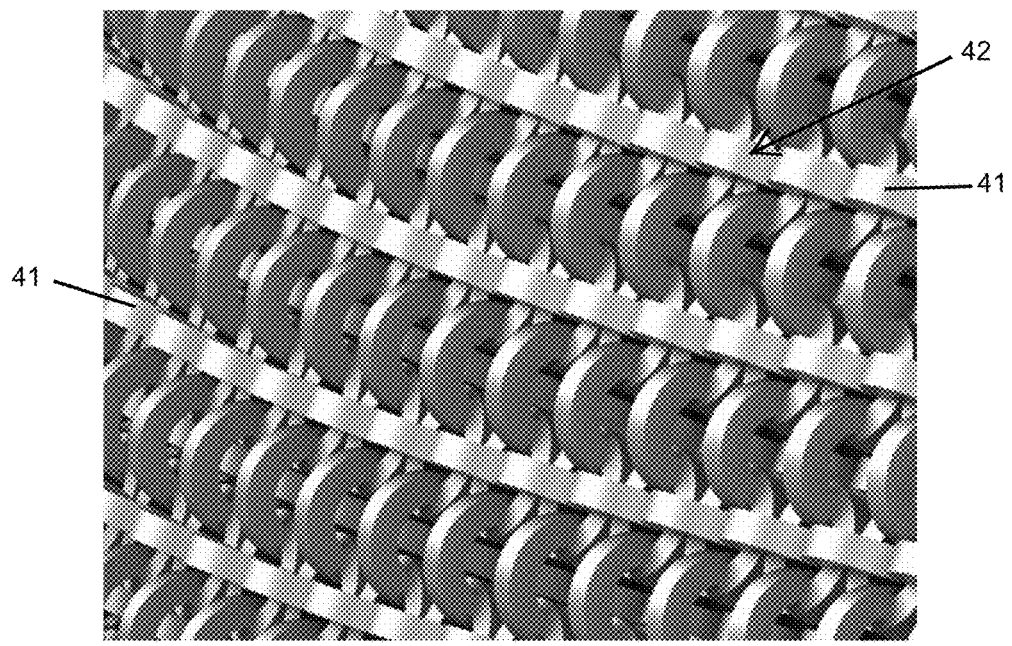

Referring again to FIGS. 1-3, the interface 40 comprises a series of interconnecting links 41. To address the need to overcome problems related to the mismatches in mechanical compliance between skin and the main body of the DSA device 10, the interface 40 incorporates gradients in: 1) mechanical compliance, ranging from a fully flexible interface, to less compliant, to a rigid interface; 2) link mobility, ranging from freely mobile to constrained; and/or, 3) porosity, ranging from highly porous to fully dense. For example, FIGS. 4A-4C show different regions of the interface 40 with varying flexibility, mobility, and porosity. FIG. 4A shows a pliant portion of the interface 40, where the links 41 are free to move relative to each other because of the large spacing within the inside diameter of any one link 41. FIG. 4B shows a less compliant region, where the space at the center of a link 41 is decreased by either increasing the thickness of a link 41 or decreasing the inner diameter of the link 41. FIG. 4C shows portions of the interface 40 that are rigid, with neighboring links fused to each other.

A gradient provides for a transition in compliance or mobility between pliable skin and the rigid prosthetic attachment post 30 and the intramedullary stem 20. In one configuration, the transition is gradual with the interface 40 rigid at a first end 43 adjacent to the stem 20 and post 30, but pliable at a second end 44 furthest from the stem 20 and post 30.

Referring again to FIG. 3, the links 41 form a chainmail scaffolding 42 to provide sites for ingrowth of skin cells and vascular tissue. In this manner, skin grows into and locks onto the chainmail scaffolding 42 from the outside surface 45, whereas vascularized soft tissues, needed to support normal skin homeostasis, grow into from the opposite (i.e. inside) surface 46 of the chainmail scaffolding 42. In one embodiment, the porosity of the scaffolding 42 becomes fully dense at the main DSA body 10 to minimize entry points for bacterial transmission. The change from porous to fully dense can be gradual or abrupt.

In an alternative configuration, a gradual change in pore size stops at a minimum pore size, then the remainder of the chainmail scaffolding 42 from this point towards the stem 20 and post 30 is fully dense. Below a certain pore size, skin may not be able to effectively grow into the pore, yet the pore is still large enough for pathogens to pass through. As such, a pore size below a critical limit is not created to prevent infiltration of pathogens in areas where skin may not be able to effectively grow to provide a protective barrier.

As previously stated, the pliant portion of the chainmail 42 consists of interconnected links 41, with each link 41 free to move relative to neighboring links 41. Because the range of movement for a link 41 is determined by the amount of free space within the interior portion (or inner diameter) of a link 41 to which it is connected, the level of link mobility can be decreased by decreasing this space. Link mobility, in turn, influences the mechanical compliance of the interface 40. For instance, portions of the chainmail scaffolding 42 can be made less compliant by decreasing an inner diameter of the link 41, thereby limiting the movement of the links 41 within that portion of the interface 40. That is, there is less open space in the interior of a link 41 having a reduced inner diameter; thus, interconnected links 41 which pass through this space are restricted in their movement. Alternatively, the thickness of each link 41 can be increased, which also restricts the range of motion between interconnected links 41.

Yet other portions of the chainmail 42 can be made stiff by building links 41 such the walls 47 of adjacent links 41 intersect and join, as shown in FIG. 4C. The structural stiffness of these joined links 41 can be varied by adjusting the link-to-link spacing, or the link 41 inner diameters, or the link 41 outer diameters, or the link 41 thicknesses, or a combination thereof. Therefore, a functional gradient in flexibility and compliance—ranging from fully flexible, to less flexible, to stiff, to rigid—can be created by selectively varying link 41 dimensions and spacings throughout the chainmail structure 42.

In the embodiment shown in FIGS. 1-3, the size of each link 41 start at 350 micron inside diameter×420 micron outside diameter×35 micron thickness at the second end 44 (furthest from the stem 20 and post 30) of the interface 40. The inside diameter of the links 41 progressively decreases and the thickness of the links 41 progressively increase, each by 12.5 microns, until the links 41 become solid discs at the first end 43 of the interface 40 next to the stem 20 and post 30. In this preferred embodiment, the center-to-center link spacing as the interface is being manufactured is 230 microns. The links 41 are radially distributed relative to a point on the axis of the stem 20 and post 30. While these dimensions are provided as examples, a person having ordinary skill in the art will appreciate that a suitable interface 40 conducive to cell growth can have different dimensions.

In alternative embodiments, the interface 40 is manufactured with different interface 40 shapes, gradient distributions, link 41 sizes, and number of layers of links 41 (i.e., number of interconnecting links 41 along radial or axial direction from the central stem 20). In addition, the cross section of the links 41 may be circular, ellipsoidal, square, rectangular, hexagonal, or other shapes. The surface of the links 41 may be micro-textured or smooth.

Figure 5:
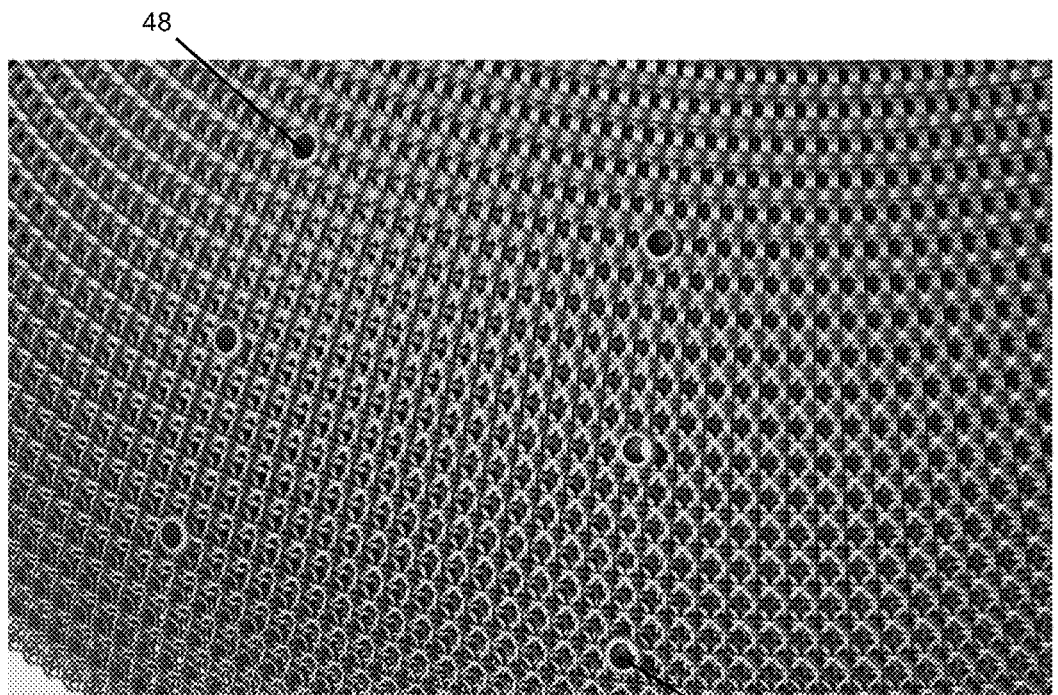
FIG. 5 shows features incorporated into the interface.

In yet another alternative embodiment, the chainmail 42 can embed other parts or features 48 with non-link geometries. For one example, FIG. 5 shows an interface 40 with chainmail 42 having through-hole features 48 distributed though the interface 40. The through-holes 48 provide another feature for skin and underlying tissue to interconnect and lock into the interface 40.

The chainmail interface 40 thus described has unique features that cannot be manufactured using traditional techniques. Therefore, another aspect of the present invention disclosed herein is a practical process to manufacture DSA devices 10 that incorporate the chainmail-based skin-to-DSA interface 40. Additionally, the method is suitable for manufacturing micro-miniature chainmail 100, which has smaller dimensions than traditional chainmail. The method is based on conventional additive manufacturing (AM) processes, but incorporates a modified chainmail 100 design to accommodate a post-processing etching step. In general, a person having ordinary skill in the art will recognize that AM processes can build-up structures of arbitrarily complex geometries in a layer-by-layer fashion.

Figure 6:
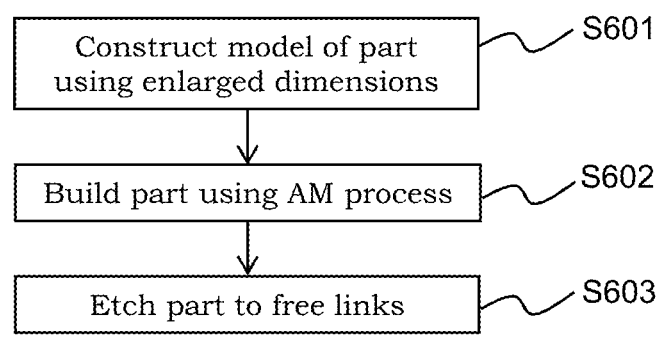
FIG. 6 is a flow diagram depicting the method of the present invention.

FIG. 6 is a flowchart showing the steps of the process. At step S601 of the process, a 3D computer-aided design (CAD) model of the part to be built is decomposed into simpler 2D cross-sectional layer descriptions to define each build layer. For one example, a CAD model of the interface 40 and DSA device 10, customized for a recipient, could first be created using data from measurements and reconstructions from MRI, CT, and/or laser scans of the recipient's residuum. As will be discussed in greater detail, the model includes dimensions that are larger than the desired final dimensions because a post-build step reduces the link 41 diameter or thickness.

At step S602, the part is manufactured using an AM process. In one embodiment, the part is constructed using a direct metal laser sintering (DMLS) process, such as the process provided by 3D Microprint GmbH. Using a DMLS process, the chainmail 100 or interface 40 and DSA device 10 can be constructed of a titanium alloy, among other materials. In this manner, each layer of the part is formed sequentially, first by depositing a thin layer of titanium alloy (Ti-6A1-4V) powder, for example, then using a high-power, highly-focused laser beam to selectively sinter or melt those regions in the layer defining the part. The process of depositing and melting the metal powder is repeated for each layer as instructed by the model created in step S601.

As is typical in AM processes, some part features may include sacrificial support structures that are simultaneously constructed with the part. For example, for the chainmail 100 or chainmail scaffolding 42 of interface 40, adjacent interconnected links 41 are free to move relative to each other. However, during construction the movable links 41 will require support structures because the links 41 would otherwise move as the powder is being deposited and leveled during the build operation at step S602. Additionally, freely moving links 41 might warp if a heat treatment is used as part of the AM process to eliminate residual stresses in the part.

With typical parts constructed in an AM process, the sacrificial support is easily removed by breaking or cutting the support away from the part at the end of the build. In this example, the support typically remains on the exterior of the part being built or is otherwise accessible for removal. On the other hand, cutting or breaking supports would not be practical or even feasible with chainmail 100 because the sacrificial supports would be interwoven with the links 41 of the chainmail 100. As such, the method of the present invention reduces or eliminates the need for such support structures by modifying the pre-build chainmail 100 design such that the links 41 are self-supporting or have minimal supporting structure.

Figure 8:
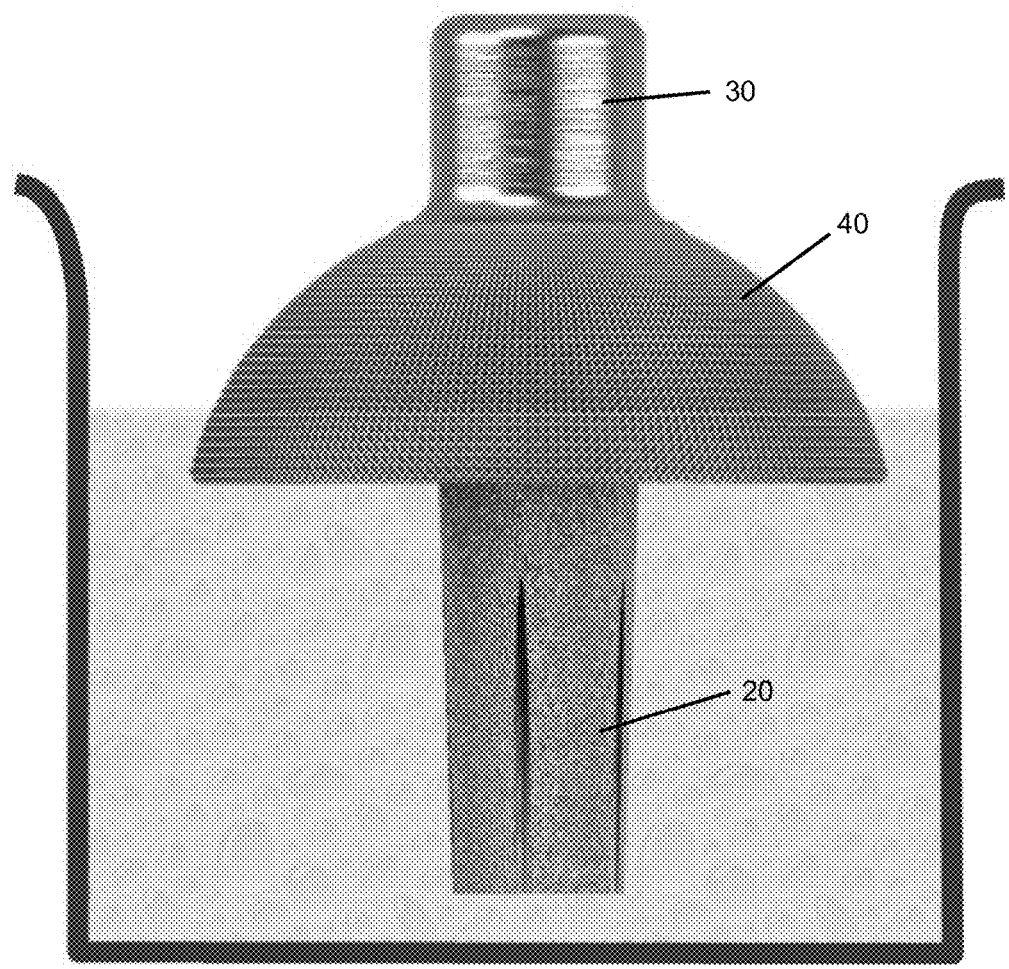
FIG. 8 shows a post-build etching process, where intersecting links of the interface, which may be fused after the additive manufacturing build process, are submerged in an etchant in order to free those links to move relative to their neighboring links.

In one configuration, links 41 ultimately intended to freely move are made thicker and forced to intersect with neighboring links 41 at their outer perimeters, thus making them self-supporting. Links 41 can be made self-supporting by reducing the link 41 inner diameter, increasing the link 41 outer diameter, or reducing the link-to-link spacing, or a combination thereof. While fusing adjoining links 41 aids the build process at step S602, the final product must include freely movable links 41. To free the fused links 41, at step 203 the part is exposed to an etchant and the outside surface of the link 41 is eroded until the links 41 have the desired dimensions and no longer intersect, freeing them to be able to move relative to their neighbors. FIG. 8 depicts a DSA device 10, with fused links 41, in an etchant.

Figure 9A:
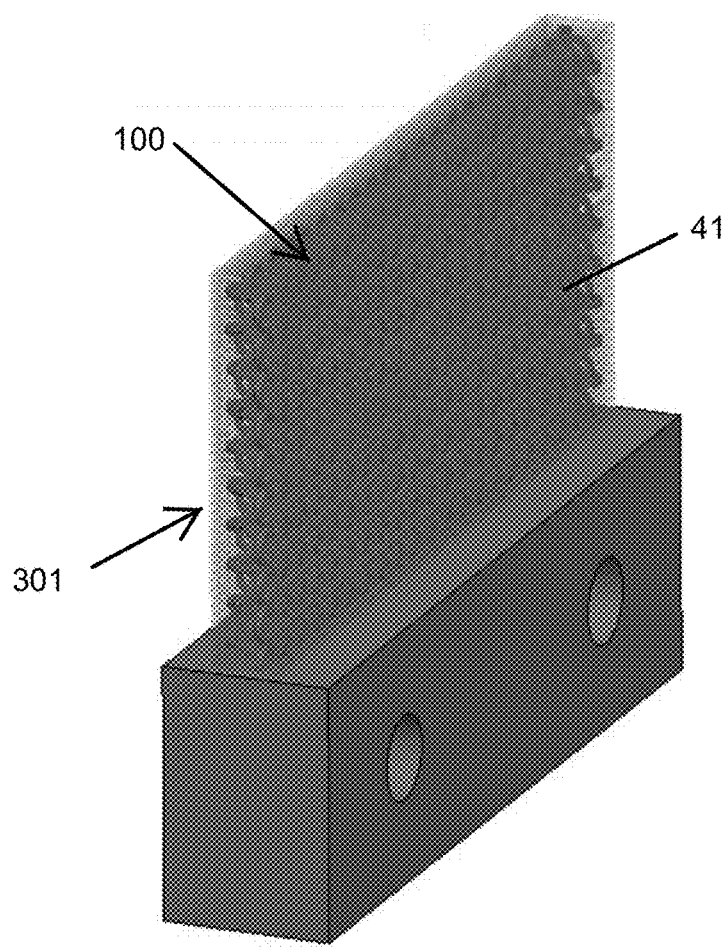
FIGS. 9A-9B show a support structure used during the additive manufacturing process to support links that are ultimately free moving.
Figure 9B:
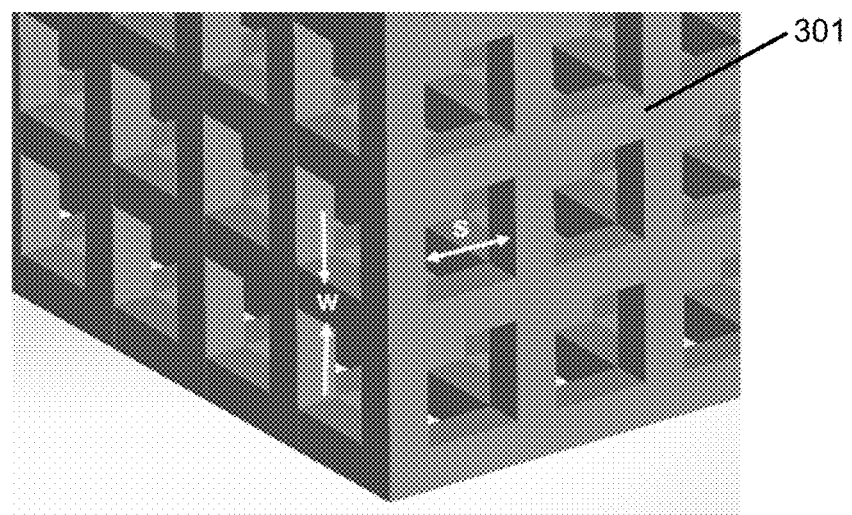

In an alternative embodiment, a minimal support structure 301 is provided to support the links 41 during the AM build process. As shown in FIGS. 9A-9B, the support structure 301 is in the shape of a lattice. In this configuration, it is important for the dimensions of the support structure 301 to remain within a range that can be removed during the etching step S603 since physical removal is not practical. Stated differently, if the etching step S603 removes 35 microns from the outside surface of the link 41, then the width of each beam in the support structure 301 should be around 35 microns or less so that it is completely removed during etching at step S603. Of course, the required dimensions of the support structure 301 depends on its dissolve rate compared to the links 41, which can be influenced by surface area and other factors.

Figure 7:
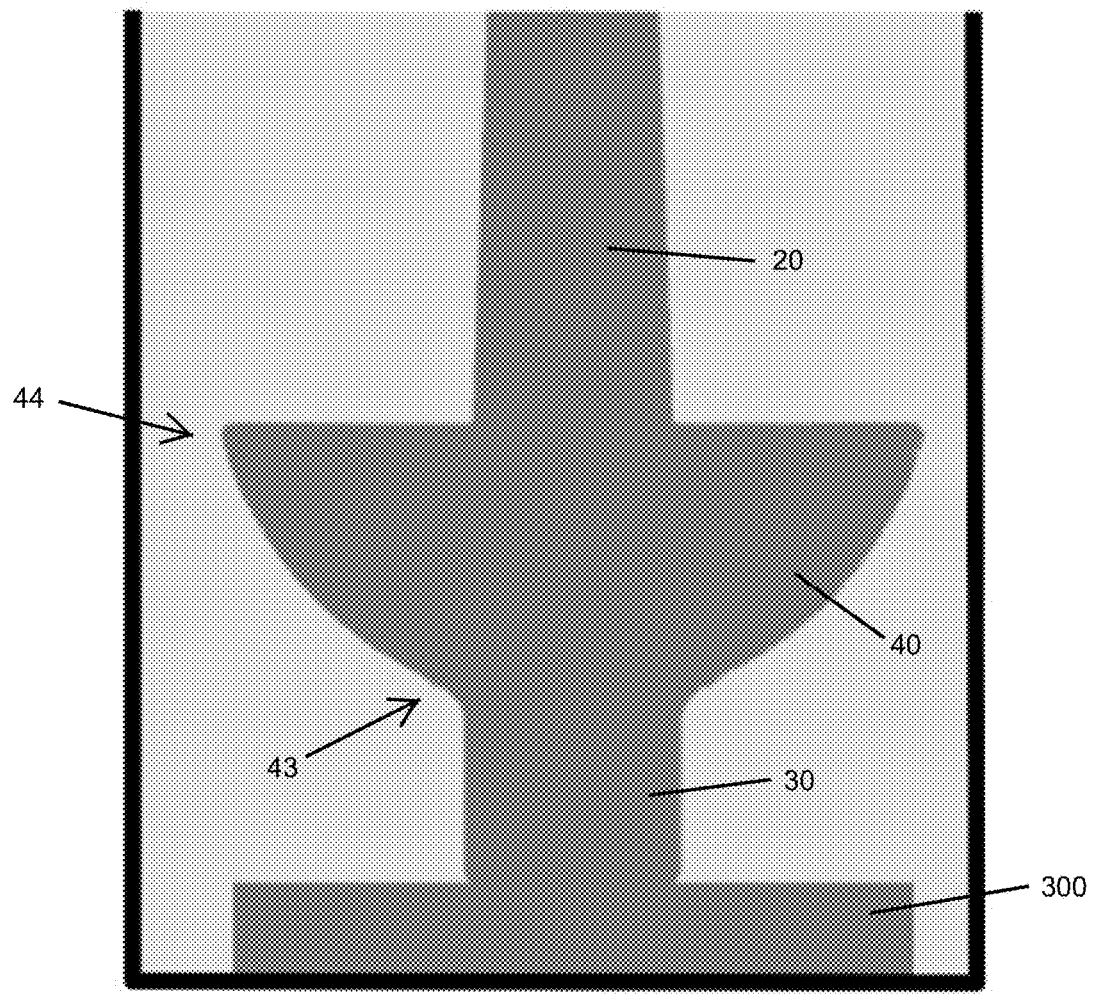
FIG. 7 shows a part built on a base using an additive manufacturing process, according to one embodiment of the invention.
Figure 10:
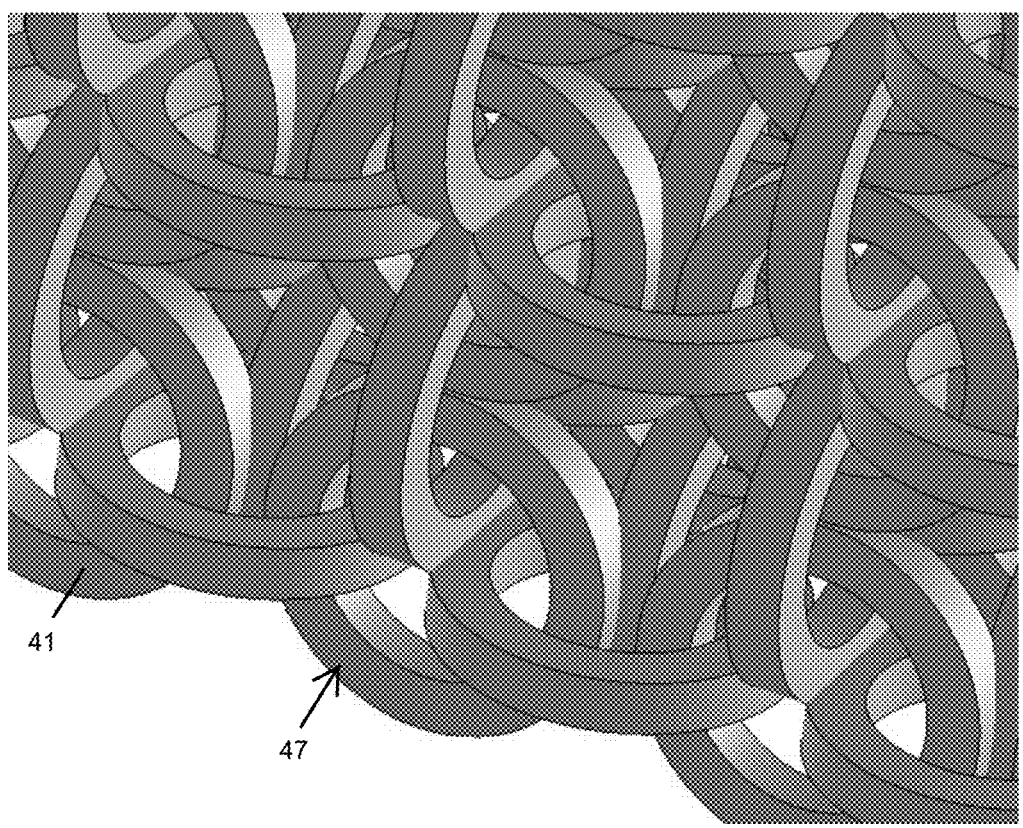
FIG. 10 is a detailed view of the interconnected links.

To accommodate the loss of material in the etching process, the pre-etch build must have larger dimensions than the desired dimensions of the finished product. By way of example, a modified pre-build computer aided design (CAD) model of the preferred embodiment is shown in FIG. 10, where the link 41 dimensions at the interface 40 are enlarged and start at 315 micron inside diameter×455 micron outside diameter×70 micron thickness. These dimensions are for a link 41 having dimensions of 350 micron inside diameter×420 micron outside diameter×35 micron thickness after etching. To create a gradient, the inside diameters are progressively decreased and the thicknesses progressively increased, each by 12.5 microns, for the next 11 rows of links 41. The remaining link 41 dimensions are not changed. In this particular example, the part is inverted and built on a base 300 (as shown in FIG. 7) to provide support for the first layer of the first row of links 41 at the first end 43 of the interface 40. After the part is completely built-up, the support base 300 on which the part is built is cut-off.

As with the previous examples, at step S603 the intersecting links 41 of the part are submerged in an etchant, for example hydrofluoric acid if the chainmail 100 were made out of Ti6A14V. The part remains in the etchant until the links 41 are eroded by 35 microns per exposed surface. At this point, the desired dimensions of the links 41 are attained and become free to move relative to each other. The part is then quickly removed from the etchant and quenched, for example, in a series of water baths.

In an alternative embodiment, the pre-build CAD model is designed with all of the links 41 the same size and intersected by the same amount of overlap. After the part is built, the entire part is submerged in an etchant and gradually removed to create a gradient in the link 41 dimensions. FIG. 7 depicts a DSA device 10 with only a portion of the links submerged in the etchant.

Similarly, in yet another alternative embodiment, a pre-build CAD model is first created where the links 41 are sized to the minimum feature size allowed by the DMLS process. The links 41 are then submerged in etchant to erode the links to the desired sizes, which can be smaller than the minimum size produced by the DMLS process. This embodiment is useful to accommodate DMLS processes with minimum feature sizes that are larger than those needed to make the chainmail 100 or interface 40.

While the disclosure has been described in detail and with reference to specific embodiments thereof, it will be apparent to one skilled in the art that various changes and modification can be made therein without departing from the spirit and scope of the embodiments. Thus, it is intended that the present disclosure cover the modifications and variations of this disclosure provided they come within the scope of the appended claims and their equivalents.

What is claimed is:

1. A direct skeletal attachment device comprising:
an intramedullary stem adapted to be inserted into a cavity of a bone;
a post adapted to interface with a prosthesis;
an interface positioned between the post and stem,
wherein the interface extends radially from a first end proximate the post and stem to a second end;
wherein the interface is rigid at the first end;
wherein the interface comprises a series of interconnected links forming a chainmail scaffolding.

2. The direct skeletal attachment of claim 1, wherein an inner diameter of each link of the series of interconnected links increases from the first end to the second end.

3. The direct skeletal attachment of claim 1, wherein a thickness of each link of the series of interconnected links decreases from the first end to the second end.

4. The direct skeletal attachment of claim 1, wherein the chainmail scaffolding has a porosity gradient.

5. The direct skeletal attachment of claim 1, wherein the chainmail scaffolding is fully dense near the stem and the post.

6. The direct skeletal attachment of claim 4, wherein a plurality of pores remain above a minimum pore diameter within the porosity gradient.

7. The direct skeletal attachment of claim 1, wherein the interface tapers from mechanically compliant at the second end to rigid at the first end.

8. The direct skeletal attachment of claim 1, wherein the links are mobile at the second end and are immobile at the first end.

* * * * *